(12) United States Patent
Wingeier

(10) Patent No.: US 9,403,020 B2
(45) Date of Patent: Aug. 2, 2016

(54) MODELING POSITIONS OF IMPLANTED DEVICES IN A PATIENT

(71) Applicant: Nevro Corporation, Menlo Park, CA (US)

(72) Inventor: Brett Wingeier, San Franisco, CA (US)

(73) Assignee: Nevro Corporation, Redwood City, CA (US)

( * ) Notice: Subject to any disclaimer, the term of this patent is extended or adjusted under 35 U.S.C. 154(b) by 0 days.

(21) Appl. No.: 13/645,387

(22) Filed: Oct. 4, 2012

(65) Prior Publication Data

US 2013/0096642 A1    Apr. 18, 2013

Related U.S. Application Data

(60) Provisional application No. 61/543,257, filed on Oct. 4, 2011, provisional application No. 61/543,766, filed on Oct. 5, 2011.

(51) Int. Cl.
*A61N 1/00* (2006.01)
*A61N 1/372* (2006.01)
(Continued)

(52) U.S. Cl.
CPC ........ *A61N 1/37211* (2013.01); *A61N 1/36071* (2013.01); *A61B 2017/00026* (2013.01); *A61B 2034/104* (2016.02); *A61B 2034/2046* (2016.02); *A61N 1/05* (2013.01); *A61N 1/0551* (2013.01)

(58) Field of Classification Search
CPC .............. A61B 5/00; A61B 5/04; A61B 5/05; A61B 5/06; A61B 5/07; A61B 5/0002; A61B 5/0033; A61B 5/0048; A61B 5/0059; A61B 5/103; A61B 5/117; A61N 1/00; A61N 1/02; A61N 1/04; A61N 1/18; A61N 1/025; A61N 1/40; A61N 1/048; A61N 1/0488; A61N 1/05; A61N 1/0504; A61N 1/0551; A61N 1/0053; A61N 1/08; A61N 2001/083
See application file for complete search history.

(56) References Cited

U.S. PATENT DOCUMENTS 3,195,540 A   7/1965 Waller
3,724,467 A   4/1973 Avery et al.
(Continued)

FOREIGN PATENT DOCUMENTS

WO   WO-2009097224 A1   8/2009
WO   WO-2011014570 A1   2/2011

OTHER PUBLICATIONS

International Search Report and Written Opinion for International Patent Application No. PCT/US12/058809, Applicant: Nevro Corporation, mailed Jan. 18, 2013, 9 pages.
(Continued)

*Primary Examiner* — Christopher D Koharski
*Assistant Examiner* — Elizabeth K So
(74) *Attorney, Agent, or Firm* — Perkins Coie LLP

(57) ABSTRACT

Technology is disclosed for modeling positions of implanted devices in a patient. In various embodiments, the technology can construct a forward model that predicts an electrical impedance between electrical contacts; detects an actual electrical impedance between electrical contacts; computes a fitness value based on a comparison between the detected electrical impedance and the predicted electrical impedance; varies at least one parameter of the forward model until the computed fitness value is a maximum fitness value; and displays at a display device a estimated position of the first lead and/or second leads.

13 Claims, 7 Drawing Sheets

(51) Int. Cl.
*A61N 1/36* (2006.01)
*A61N 1/05* (2006.01)
*A61B 17/00* (2006.01)

(56) References Cited

U.S. PATENT DOCUMENTS

| | | | |
|---|---|---|---|
| 3,796,221 A | 3/1974 | Hagfors |
| 4,096,866 A | 6/1978 | Fischell |
| 4,282,886 A | 8/1981 | King |
| 4,498,482 A | 2/1985 | Williams |
| 4,515,168 A | 5/1985 | Chester et al. |
| 4,796,642 A | 1/1989 | Harris |
| 5,042,486 A | 8/1991 | Pfeiler et al. |
| 5,078,140 A | 1/1992 | Kwoh |
| 5,159,926 A | 11/1992 | Ljungstroem |
| 5,211,165 A | 5/1993 | Dumoulin et al. |
| 5,257,636 A | 11/1993 | White |
| 5,325,873 A | 7/1994 | Hirschi et al. |
| 5,351,697 A | 10/1994 | Cheney et al. |
| 5,375,596 A | 12/1994 | Twiss et al. |
| 5,425,367 A | 6/1995 | Shapiro et al. |
| 5,727,553 A | 3/1998 | Saad |
| 5,769,877 A | 6/1998 | Barreras, Sr. |
| 5,848,126 A | 12/1998 | Fujita et al. |
| 5,871,487 A | 2/1999 | Warner et al. |
| 6,106,460 A | 8/2000 | Panescu et al. |
| 6,198,963 B1 | 3/2001 | Haim et al. |
| 6,214,016 B1 | 4/2001 | Williams et al. |
| 6,216,045 B1 | 4/2001 | Black et al. |
| 6,263,230 B1 | 7/2001 | Haynor et al. |
| 6,292,702 B1 | 9/2001 | King et al. |
| 6,308,103 B1 | 10/2001 | Gielen |
| 6,309,401 B1 | 10/2001 | Redko et al. |
| 6,321,104 B1 | 11/2001 | Gielen et al. |
| 6,321,123 B1 | 11/2001 | Morris et al. |
| 6,366,815 B1 | 4/2002 | Haugland et al. |
| 6,397,108 B1 | 5/2002 | Camps et al. |
| 6,442,435 B2 | 8/2002 | King et al. |
| 6,445,955 B1 | 9/2002 | Michelson et al. |
| 6,464,682 B1 | 10/2002 | Snoke |
| 6,474,341 B1 | 11/2002 | Hunter et al. |
| 6,477,427 B1 | 11/2002 | Stolz et al. |
| 6,493,592 B1 | 12/2002 | Leonard et al. |
| 6,516,807 B1 | 2/2003 | Panescu et al. |
| 6,522,932 B1 | 2/2003 | Kuzma et al. |
| 6,529,774 B1 | 3/2003 | Greene |
| 6,549,797 B1 | 4/2003 | Leonard et al. |
| 6,549,812 B1 | 4/2003 | Smits |
| 6,556,873 B1 | 4/2003 | Smits |
| 6,560,491 B1 | 5/2003 | Leonard et al. |
| 6,600,956 B2 | 7/2003 | Maschino et al. |
| 6,609,029 B1 | 8/2003 | Mann et al. |
| 6,622,051 B1 | 9/2003 | Bishay et al. |
| 6,718,211 B2 | 4/2004 | Smits |
| 6,721,604 B1 | 4/2004 | Robinson et al. |
| 6,741,892 B1 | 5/2004 | Meadows et al. |
| 6,741,893 B2 | 5/2004 | Smits |
| 6,847,845 B2 | 1/2005 | Belden |
| 6,875,571 B2 | 4/2005 | Crabtree et al. |
| 6,895,283 B2 | 5/2005 | Erickson et al. |
| 6,907,299 B2 | 6/2005 | Han |
| 6,909,918 B2 | 6/2005 | Stypulkowski |
| 6,934,589 B2 | 8/2005 | Sundquist et al. |
| 6,970,747 B2 | 11/2005 | Kokones et al. |
| 6,993,384 B2 | 1/2006 | Bradley et al. |
| 7,010,856 B2 | 3/2006 | Suda et al. |
| 7,047,082 B1 | 5/2006 | Schrom et al. |
| 7,051,419 B2 | 5/2006 | Schrom et al. |
| 7,072,719 B2 | 7/2006 | Vinup et al. |
| 7,107,104 B2 | 9/2006 | Keravel et al. |
| 7,110,827 B2 | 9/2006 | Sage et al. |
| 7,130,696 B2 | 10/2006 | Carter et al. |
| 7,133,722 B2 | 11/2006 | Hansen et al. |
| 7,142,919 B2 | 11/2006 | Hine et al. |
| 7,149,585 B2 | 12/2006 | Wessman et al. |
| 7,164,951 B2 | 1/2007 | Ries et al. |
| 7,174,219 B2 | 2/2007 | Wahlstrand et al. |
| 7,184,838 B2 | 2/2007 | Cross, Jr. |
| 7,184,840 B2 | 2/2007 | Stolz et al. |
| 7,187,981 B2 | 3/2007 | Tanaka |
| 7,211,103 B2 | 5/2007 | Greenberg et al. |
| 7,212,867 B2 | 5/2007 | Van Venrooij et al. |
| 7,244,150 B1 | 7/2007 | Brase et al. |
| 7,282,033 B2 | 10/2007 | Urmey |
| 7,363,089 B2 | 4/2008 | Vinup et al. |
| 7,386,350 B2 | 6/2008 | Vilims |
| 7,421,297 B2 | 9/2008 | Giftakis et al. |
| 7,455,666 B2 | 11/2008 | Purdy |
| 7,463,917 B2 | 12/2008 | Martinez |
| 7,493,159 B2 | 2/2009 | Hrdlicka et al. |
| 7,499,755 B2 | 3/2009 | Cross, Jr. |
| 7,502,652 B2 | 3/2009 | Gaunt et al. |
| 7,584,004 B2 | 9/2009 | Caparso et al. |
| 7,613,524 B2 | 11/2009 | Jordan |
| 7,617,003 B2 | 11/2009 | Caparso et al. |
| 7,623,919 B2 | 11/2009 | Goetz et al. |
| 7,689,284 B2 | 3/2010 | Imran et al. |
| 7,702,379 B2 | 4/2010 | Avinash et al. |
| 7,769,472 B2 | 8/2010 | Gerber |
| 7,781,806 B2 | 8/2010 | VanBuskirk et al. |
| 7,810,233 B2 | 10/2010 | Krulevitch et al. |
| 7,810,996 B1 | 10/2010 | Giphart et al. |
| 7,831,307 B1 | 11/2010 | Moffitt |
| 7,844,343 B2 | 11/2010 | Wahlstrand et al. |
| 7,853,330 B2 | 12/2010 | Bradley et al. |
| 7,860,568 B2 | 12/2010 | Deininger et al. |
| 7,881,806 B2 | 2/2011 | Horrigan et al. |
| 7,996,055 B2 | 8/2011 | Hauck et al. |
| 8,019,439 B2 | 9/2011 | Kuzma et al. |
| 8,060,207 B2 | 11/2011 | Wallace et al. |
| 8,078,280 B2 | 12/2011 | Sage |
| 8,131,357 B2 | 3/2012 | Bradley et al. |
| 8,197,494 B2 | 6/2012 | Jaggi et al. |
| 8,303,502 B2 | 11/2012 | Washburn et al. |
| 8,355,791 B2 | 1/2013 | Moffitt |
| 8,355,797 B2 | 1/2013 | Caparso et al. |
| 8,494,652 B2 | 7/2013 | Cantlon et al. |
| 8,676,331 B2 | 3/2014 | Parker |
| 9,002,460 B2 | 4/2015 | Parker |
| 2001/0025192 A1 | 9/2001 | Gerber et al. |
| 2001/0053885 A1 * | 12/2001 | Gielen et al. ............ 604/20 |
| 2002/0111661 A1 | 8/2002 | Cross et al. |
| 2002/0173718 A1 | 11/2002 | Frisch et al. |
| 2002/0177887 A1 | 11/2002 | Krebs |
| 2003/0032997 A1 | 2/2003 | Pianca et al. |
| 2003/0055476 A1 | 3/2003 | Vinup et al. |
| 2003/0083697 A1 | 5/2003 | Baudino et al. |
| 2003/0097165 A1 | 5/2003 | Krulevitch et al. |
| 2003/0097166 A1 | 5/2003 | Krulevitch et al. |
| 2003/0114752 A1 | 6/2003 | Henderson et al. |
| 2003/0120150 A1 | 6/2003 | Govari |
| 2003/0136418 A1 | 7/2003 | Behm |
| 2003/0199953 A1 | 10/2003 | Stolz et al. |
| 2003/0199962 A1 | 10/2003 | Struble et al. |
| 2003/0208247 A1 | 11/2003 | Spinelli et al. |
| 2003/0229387 A1 | 12/2003 | Cross et al. |
| 2003/0233134 A1 | 12/2003 | Greenberg et al. |
| 2004/0015205 A1 | 1/2004 | Whitehurst et al. |
| 2004/0024439 A1 | 2/2004 | Riso |
| 2004/0024440 A1 | 2/2004 | Cole |
| 2004/0087877 A1 | 5/2004 | Besz et al. |
| 2004/0088033 A1 | 5/2004 | Smits et al. |
| 2004/0097803 A1 | 5/2004 | Panescu |
| 2004/0111139 A1 | 6/2004 | McCreery |
| 2004/0127942 A1 | 7/2004 | Yomtov et al. |
| 2004/0162601 A1 | 8/2004 | Smits |
| 2004/0176683 A1 | 9/2004 | Whitin et al. |
| 2004/0186543 A1 | 9/2004 | King et al. |
| 2004/0186544 A1 | 9/2004 | King |
| 2004/0215305 A1 | 10/2004 | Sage |
| 2004/0215307 A1 | 10/2004 | Michels et al. |
| 2004/0243206 A1 | 12/2004 | Tadlock |
| 2005/0004638 A1 | 1/2005 | Cross |
| 2005/0004639 A1 | 1/2005 | Erickson |

(56) References Cited

U.S. PATENT DOCUMENTS

| | | |
|---|---|---|
| 2005/0015128 A1 | 1/2005 | Rezai et al. |
| 2005/0027341 A1 | 2/2005 | Schrom et al. |
| 2005/0033371 A1 | 2/2005 | Sommer et al. |
| 2005/0049486 A1 | 3/2005 | Urquhart et al. |
| 2005/0049663 A1 | 3/2005 | Harris et al. |
| 2005/0049664 A1 | 3/2005 | Harris et al. |
| 2005/0065588 A1 | 3/2005 | Zhao et al. |
| 2005/0070982 A1 | 3/2005 | Heruth et al. |
| 2005/0075684 A1 | 4/2005 | Phillips et al. |
| 2005/0075707 A1 | 4/2005 | Meadows et al. |
| 2005/0085870 A1 | 4/2005 | Goroszeniuk |
| 2005/0107859 A1 | 5/2005 | Daglow et al. |
| 2005/0119713 A1 | 6/2005 | Whitehurst et al. |
| 2005/0131506 A1 | 6/2005 | Rezai et al. |
| 2005/0138791 A1 | 6/2005 | Black et al. |
| 2005/0138792 A1 | 6/2005 | Black et al. |
| 2005/0171587 A1 | 8/2005 | Daglow et al. |
| 2005/0203599 A1 | 9/2005 | Garabedian et al. |
| 2005/0209667 A1 | 9/2005 | Erickson et al. |
| 2005/0222658 A1 | 10/2005 | Hoegh et al. |
| 2005/0222659 A1 | 10/2005 | Olsen et al. |
| 2005/0228221 A1 | 10/2005 | Hirakawa |
| 2005/0246003 A1 | 11/2005 | Black et al. |
| 2005/0246004 A1 | 11/2005 | Cameron et al. |
| 2006/0004429 A1 | 1/2006 | Mrva et al. |
| 2006/0052765 A1 | 3/2006 | Pyles et al. |
| 2006/0089696 A1 | 4/2006 | Olsen et al. |
| 2006/0089697 A1 | 4/2006 | Cross et al. |
| 2006/0111768 A1 | 5/2006 | Wessman et al. |
| 2006/0127158 A1 | 6/2006 | Olson et al. |
| 2006/0168805 A1 | 8/2006 | Hegland et al. |
| 2006/0200218 A1 | 9/2006 | Wahlstrand |
| 2006/0247748 A1 | 11/2006 | Wahlstrand et al. |
| 2006/0247749 A1 | 11/2006 | Colvin |
| 2006/0265024 A1 | 11/2006 | Goetz et al. |
| 2006/0271137 A1 | 11/2006 | Stanton-Hicks |
| 2007/0032836 A1 | 2/2007 | Thrope et al. |
| 2007/0038052 A1 | 2/2007 | Swoyer et al. |
| 2007/0050004 A1 | 3/2007 | Swoyer et al. |
| 2007/0055332 A1 | 3/2007 | Swoyer |
| 2007/0088414 A1 | 4/2007 | Campbell et al. |
| 2007/0100386 A1 | 5/2007 | Tronnes et al. |
| 2007/0100391 A1 | 5/2007 | Armstrong |
| 2007/0100408 A1 | 5/2007 | Gerber |
| 2007/0106144 A1 | 5/2007 | Squeri |
| 2007/0106289 A1 | 5/2007 | O'Sullivan |
| 2007/0106339 A1 | 5/2007 | Errico et al. |
| 2007/0112398 A1 | 5/2007 | Stevenson et al. |
| 2007/0112404 A1 | 5/2007 | Mann et al. |
| 2007/0118198 A1 | 5/2007 | Prager |
| 2007/0135881 A1 | 6/2007 | Vilims |
| 2007/0149048 A1 | 6/2007 | O'Brien et al. |
| 2007/0150026 A1 | 6/2007 | Bourget et al. |
| 2007/0150036 A1 | 6/2007 | Anderson |
| 2007/0191709 A1 | 8/2007 | Swanson |
| 2007/0191904 A1 | 8/2007 | Libbus et al. |
| 2007/0191909 A1 | 8/2007 | Ameri et al. |
| 2007/0203540 A1 | 8/2007 | Goetz et al. |
| 2007/0208394 A1 | 9/2007 | King et al. |
| 2007/0249901 A1 | 10/2007 | Ohline et al. |
| 2007/0260290 A1 | 11/2007 | Hara et al. |
| 2008/0039738 A1 | 2/2008 | Dinsmoor et al. |
| 2008/0058875 A1 | 3/2008 | Greenberg et al. |
| 2008/0097475 A1 | 4/2008 | Jaggi et al. |
| 2008/0125833 A1 | 5/2008 | Bradley et al. |
| 2008/0140087 A1 | 6/2008 | Barbagli |
| 2008/0140152 A1 | 6/2008 | Imran et al. |
| 2008/0183221 A1 | 7/2008 | Burdulis |
| 2008/0234791 A1 | 9/2008 | Arle et al. |
| 2008/0275467 A1 | 11/2008 | Liao et al. |
| 2008/0319311 A1 | 12/2008 | Hamadeh |
| 2009/0024187 A1 | 1/2009 | Erickson et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0210029 A1 | 8/2009 | Tsui |
| 2009/0248118 A1 | 10/2009 | Bradley et al. |
| 2009/0270940 A1 | 10/2009 | Deininger et al. |
| 2009/0319013 A1 | 12/2009 | Boling et al. |
| 2010/0069736 A1 | 3/2010 | Finneran et al. |
| 2010/0137944 A1 | 6/2010 | Zhu |
| 2010/0137955 A1 | 6/2010 | Milijasevic et al. |
| 2010/0152538 A1 | 6/2010 | Gleason et al. |
| 2010/0191307 A1 | 7/2010 | Fang et al. |
| 2010/0204569 A1 | 8/2010 | Burnside et al. |
| 2010/0211135 A1 | 8/2010 | Caparso et al. |
| 2010/0274312 A1 | 10/2010 | Alataris et al. |
| 2010/0274314 A1 | 10/2010 | Alataris et al. |
| 2010/0274316 A1 | 10/2010 | Alataris et al. |
| 2010/0274326 A1 | 10/2010 | Chitre et al. |
| 2010/0274336 A1 | 10/2010 | Nguyen-Stella et al. |
| 2010/0286551 A1 | 11/2010 | Harlev et al. |
| 2010/0298905 A1 | 11/2010 | Simon |
| 2010/0305631 A1 | 12/2010 | Bradley et al. |
| 2010/0324414 A1 | 12/2010 | Harlev et al. |
| 2011/0009927 A1 | 1/2011 | Parker et al. |
| 2011/0031961 A1 | 2/2011 | Durand et al. |
| 2011/0046617 A1 | 2/2011 | Thompson et al. |
| 2011/0071593 A1 | 3/2011 | Parker et al. |
| 2011/0106052 A1 | 5/2011 | Chiang et al. |
| 2011/0160568 A1 | 6/2011 | Seeley et al. |
| 2012/0083709 A1 | 4/2012 | Parker et al. |
| 2012/0083856 A1 | 4/2012 | Thacker et al. |
| 2012/0172946 A1 | 7/2012 | Alataris et al. |
| 2013/0066411 A1 | 3/2013 | Thacker et al. |
| 2013/0116754 A1 | 5/2013 | Sharma et al. |
| 2013/0261697 A1 | 10/2013 | Walker |
| 2015/0012077 A1 | 1/2015 | Parker et al. |

OTHER PUBLICATIONS

Kulkarni et al., "A two-layered forward model of tissue for electrical impedance tomography," Physiol Meas., 30(6): pp. 1-24, Jun. 2009.
U.S. Appl. No. 13/607,617, filed Sep. 17, 2012, Thacker.
U.S. Appl. No. 14/167,968, filed Jan. 29, 2014, Parker.
European Extended Search Report for European Patent Application No. 12838699, Applicant: Nevro Corporation, mailed Jul. 8, 2015, 8 pages.

* cited by examiner

MODELING POSITIONS OF IMPLANTED DEVICES IN A PATIENT

CROSS-REFERENCE TO RELATED APPLICATION

This application claims the benefit to U.S. Provisional Patent Application No. 61/543,257, filed Oct. 4, 2011, entitled "MODELING POSITIONS OF IMPLANTED DEVICES IN A PATIENT," and U.S. Provisional Patent Application No. 61/543,766, filed Oct. 5, 2011, entitled "MODELING POSITIONS OF IMPLANTED DEVICES IN A PATIENT," each of which is incorporated herein by reference in its entirety.

This application is related to U.S. patent application Ser. No. 12/895,403, entitled "SYSTEMS AND METHODS FOR POSITIONING IMPLANTED DEVICES IN A PATIENT", and filed on Sep. 30, 2010, which Application is incorporated herein by reference in its entirety.

The following patent applications are incorporated herein by reference in their entireties: U.S. application Ser. No. 12/468,688, filed May 19, 2009 and titled IMPLANTABLE NEURAL STIMULATION ELECTRODE ASSEMBLIES AND METHODS FOR STIMULATING SPINAL NEURAL SITES U.S. application Ser. No. 12/362,244, filed Jan. 29, 2009 and titled SYSTEMS AND METHODS FOR PRODUCING ASYNCHRONOUS NEURAL RESPONSES TO TREAT PAIN AND/OR OTHER PATIENT CONDITIONS; U.S. application Ser. No. 12/499,769, filed Jul. 8, 2009 and titled SYSTEMS AND METHODS FOR ADJUSTING ELECTRICAL THERAPY BASED ON IMPEDANCE CHANGES; U.S. application Ser. No. 12/765,685, filed Apr. 22, 2010 and titled SPINAL CORD MODULATION FOR INDUCING PARESTHETIC AND ANESTHETIC EFFECTS, AND ASSOCIATED SYSTEMS AND METHODS; U.S. application Ser. No. 12/765,747, filed Apr. 22, 2010 and titled SELECTIVE HIGH FREQUENCY SPINAL CORD MODULATION FOR INHIBITING PAIN WITH REDUCED SIDE EFFECTS, AND ASSOCIATED SYSTEMS AND METHODS; U.S. application Ser. No. 12/765,790, filed Apr. 22, 2010 and titled DEVICES FOR CONTROLLING HIGH FREQUENCY SPINAL CORD MODULATION FOR INHIBITING PAIN, AND ASSOCIATED SYSTEMS AND METHODS, INCLUDING SIMPLIFIED CONTROLLERS; U.S. Provisional Application No. 61/418,379, filed Nov. 30, 2010 and titled EXTENDED PAIN RELIEF VIA HIGH FREQUENCY SPINAL CORD MODULATION, AND ASSOCIATED SYSTEMS AND METHODS; U.S. application Ser. No. 12/264,836, filed Nov. 4, 2008 and titled MULTI-FREQUENCY NEURAL TREATMENTS AND ASSOCIATED SYSTEMS AND METHODS; and U.S. application Ser. No. 13/607,617, filed Sep. 7, 2012 and titled SELECTIVE HIGH FREQUENCY SPINAL CORD MODULATION FOR INHIBITING PAIN, INCLUDING CEPHALIC AND/OR TOTAL BODY PAIN WITH REDUCED SIDE EFFECTS, AND ASSOCIATED SYSTEMS AND METHODS.

TECHNICAL FIELD

The disclosed technology is directed generally to modeling positions of implanted devices in a patient.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and multiple conductive rings spaced apart from each other at the distal end of the lead body. The conductive rings operate as individual electrodes and the SCS leads are typically implanted by practitioners either surgically or percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. During pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. In other cases, the patients can report pain relief without paresthesia or other sensations.

In any of the foregoing neurological stimulation systems, it is important for the practitioners to accurately position the stimulator to provide effective therapy. One approach to accurately positioning the stimulator is to implant the stimulator in a surgical procedure so that the practitioner has a clear visual access to the implantation site. However, many patients and practitioners wish to avoid the invasiveness and associated likelihood for complications typical of a surgical procedure. Accordingly, many patients and practitioners prefer a less invasive (e.g., percutaneous) implantation technique. With a percutaneous approach, the practitioner typically is unable to see exactly where the device is positioned because the device is beneath the patient's skin and, in most SCS cases, is within the patient's spinal column. In addition, the process typically requires the patient to provide feedback to the practitioner based on that patient's sensations. Accordingly, the industry has developed a variety of techniques for visualizing medical devices and anatomical features below the patient's skin. Such techniques include fluoroscopy, which is commonly used to aid the practitioner when implanting SCS leads. However, a drawback with fluoroscopy is that it results in added expense to the SCS implantation procedure, it may be cumbersome to implement, it limits the implantation procedure to sites with fluoroscopy equipment, and it exposes the patient to unwanted x-ray radiation.

DETAILED DESCRIPTION

Figure 1A:
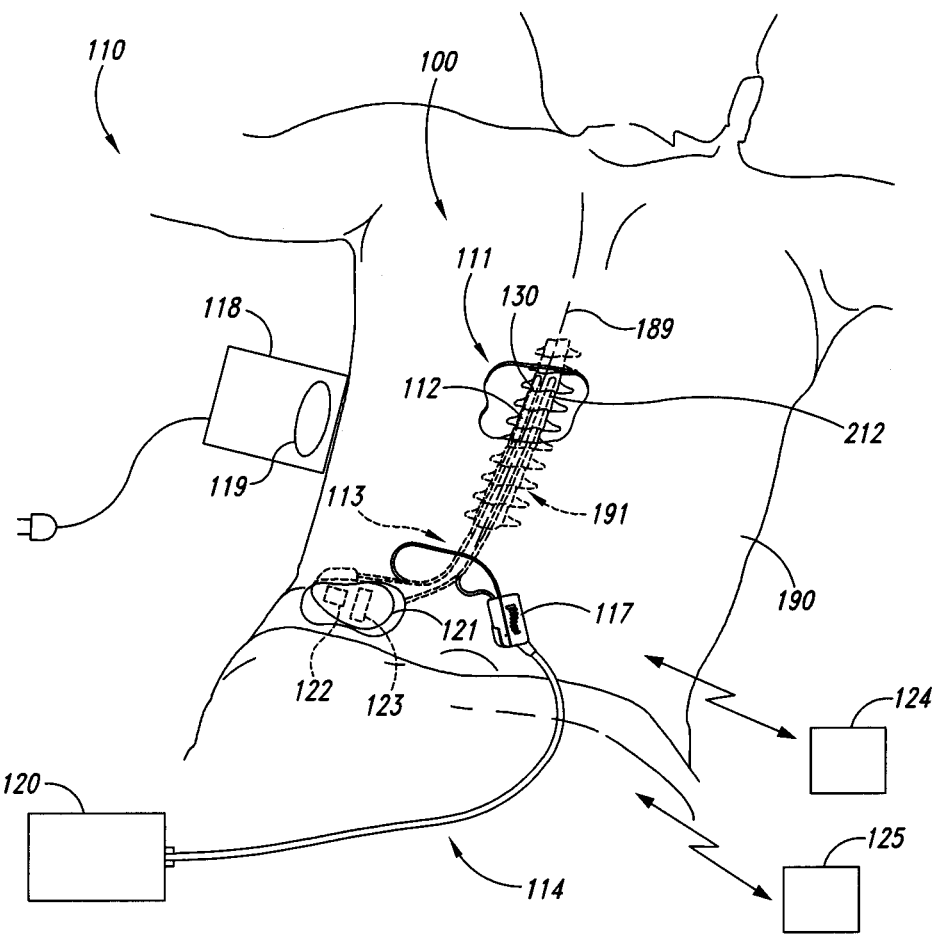
FIG. 1A is a partially schematic illustration of an implantable spinal cord modulation system positioned at a patient's spine to deliver therapeutic signals in accordance with several embodiments of the present disclosure.

The disclosed technology is directed generally to modeling positions of implanted devices in a patient. In various embodiments, the technology is used to assist a practitioner implanting leads proximate to a patient's spinal cord to deliver high frequency signals that modulate neural activity at the patient's spine, e.g., to address chronic pain. In other embodiments, however, the systems and associated methods can have different configurations, components, procedures and/or purposes. Still other embodiments may eliminate particular components or procedures. A person of ordinary skill in the relevant art, therefore, will understand that the technology may include other embodiments with additional elements, and/or may include other embodiments without several of the features shown and described below with reference to the Figures. The technology estimates the relative positions of leads positioned in the fatty epidural space dorsal to the spinal cord and within the spine of the patient. By modeling impedances between multiple contacts (e.g., electrical contacts) on each lead, computing a fitness value to represent similarity between an output of the model and measured impedances, and attempting to maximize the fitness value, the technology can accurately determine the relative positions of leads.

In various embodiments, an implanted stimulation system includes two leads and each lead may have eight contacts. By modulating electrical signals at the leads and/or contacts, the implanted stimulation system can reduce pain that a patient experiences, e.g., in the patient's spinal cord area. In other embodiments, more or fewer leads and/or contacts may be employed. In various embodiments, the technology can detect impedances between contacts, e.g., between any two specified contacts. In other embodiments, the technology can detect impedances of paths between any two poles. A pole is a set of one or more contacts connected electrically and functioning as a unit. In these embodiments, the casing or other electrically conductive components of the stimulation system may be used as contacts. The technology can assume that impedance along a given path is a function of a three-dimensional Cartesian length of the path, e.g., a sum of the impedance of the path through tissue plus one or more impedance values characteristic to the electrode-tissue interface at the contacts involved in the path. In other embodiments, other models of impedance may be employed. The technology constructs a model (e.g., a "forward model") of the expected impedance measured between contacts of the two leads, e.g., between contact of a first lead and each contact of a second lead. The model can take as input various parameters, e.g., geometric parameters such as distances between the two leads at various points, rotation about axes, etc; various physical parameters such as resistivity or specific impedance of nearby tissue; and parameters representing impedance values at each contact. The impedance value for each contact is the impedance of an electrode-tissue interface at that contact. The model can then output a set of predicted impedance measurements. The technology can then compute a fitness value that compares the output of the model with actually detected impedance values. In other embodiments, the technology can compute a distance value that expresses the difference between the output of the model and the actually detected impedance values. By employing techniques for varying the inputs, producing outputs, and maximizing a computed fitness value or minimizing a computed distance value, the technology can accurately detect the relative position of leads. Values for some or all parameters (e.g., geometric parameters) representing the detected relative position can be drawn from a continuous range of values, e.g., a range of possible values that are not limited to discrete or predetermined values. Thus, the technology employs the forward model to compute the position of leads without requiring predetermined positions for the leads and without requiring precalculated impedance measurement predictions for these predetermined positions.

In various embodiments, the forward model can be used to optimize the position of the leads. As an example, a practitioner may attempt to locate an optimal position for the leads, e.g., to minimize patient discomfort. The technology can employ the forward model to predict the relative position of leads, e.g., at some point in the future. As an example, by analyzing the vectors of movement of the leads, the technology can guide the practitioner, e.g., by displaying on a screen the predicted positions of the leads. The technology may determine this predicted position by assuming a constant direction and rate of movement and calculating the expected position if the direction and rate were to remain constant. As another example, a prediction of lead position based on previous lead movement data may be used to provide constraints, starting values, or historical comparisons for estimates of current lead position using the technology described herein. This previous lead movement data may include lead positions estimated from impedance or other measurements, lead positions directly measured using fluoroscopy or other techniques, or a combination of these data sources.

Several embodiments of the technology are described in more detail in reference to the Figures. The computing devices on which the described technology may be implemented may include one or more central processing units, memory, input devices (e.g., keyboard and pointing devices), output devices (e.g., display devices), storage devices (e.g., memory, disk drives, etc.), and network devices (e.g., network interfaces). The memory and storage devices are computer-readable media that may store instructions that implement aspects of the disclosed technology. These memory and storage devices may be tangible and/or non-transitory in various embodiments. In addition, the data structures and message structures may be stored or transmitted via a data transmission medium, such as a signal on a communications link. Various communications links may be used for computing devices to communicate, such as the Internet, a local area network, a wide area network, or a point-to-point dial-up connection.

FIG. 1A schematically illustrates a representative patient system 100 for providing relief from chronic pain and/or other conditions, arranged relative to the general anatomy of a patient's spinal cord 191. The overall patient system 100 can include a signal delivery system 110, which may be implanted within a patient 190, typically at or near the patient's midline 189, and coupled to a pulse generator/receiver 121. The signal delivery system 110 can provide therapeutic electrical signals to the patient during operation. The overall patient system 100 can further include a signal transmission system 130. The signals handled by the signal transmission system 130 can function to identify the location of the signal delivery system 110 and/or deliver relief from pain. Accordingly, the signal transmission system 130 can operate independently of the signal delivery system 110 to guide the practitioner as he/she positions elements of the signal delivery system 110 within the patient. Nevertheless, in particular embodiments, certain elements of the signal transmission system 130 can be shared with the signal delivery system 110. Aspects of the signal delivery system 110 are described immediately below. In some embodiments, the signal transmission system is absent.

In various embodiments, the signal delivery system 110 includes a signal delivery device 111 that includes features for delivering therapy to the patient 190 after implantation. The pulse generator/receiver 121 can be connected directly to the signal delivery device 111, or it can be coupled to the signal delivery device 111 via a signal link 113 (e.g., an extension). In various embodiments, the signal delivery device 111 can include elongated leads or lead bodies 112 and 212. As used herein, the terms "lead" and "lead body" include any of a number of suitable substrates and/or support members that carry devices for providing therapy signals to the patient 190. For example, the lead 112 can include one or more electrical contacts (e.g., electrodes) that direct electrical signals into the patient's tissue, such as to provide for patient relief. In other embodiments, the signal delivery device 111 can include structures other than a lead body (e.g., a paddle) that also direct electrical signals and/or other types of signals to the patient 190. In various embodiments, lead 112 delivers signals and lead 212 detects the delivered signals. In other embodiments, both leads 112 and 212 deliver signals.

The pulse generator/receiver 121 can transmit signals (e.g., electrical signals) to the signal delivery device 111 that up-regulate (e.g., stimulate or excite) and/or down-regulate (e.g., block or suppress) target nerves. As used herein, and unless otherwise noted, the terms "modulate" and "modulation" refer generally to signals that have either type of the foregoing effects on the target nerves. The pulse generator/receiver 121 can include a computing device with instructions for generating and transmitting suitable therapy signals. The pulse generator/receiver 121 and/or other elements of the system 100 can include one or more processors 122, memories or other storage devices 123 and/or input/output devices. Accordingly, the process of providing modulation signals, providing guidance information for locating the signal delivery device 111, and/or executing other associated functions can be performed by computer-executable instructions stored in computer-readable media or storage devices (e.g., memory) located at the pulse generator/receiver 121 and/or other system components. The pulse generator/receiver 121 can include multiple portions, elements, and/or subsystems (e.g., for directing signals in accordance with multiple signal delivery parameters), carried in a single housing, as shown in FIG. 1A, or in multiple housings.

In some embodiments, the pulse generator/receiver 121 can obtain power to generate the therapy signals from an external power source 118. The external power source 118 can transmit power to the implanted pulse generator/receiver 121 using electromagnetic induction (e.g., RF signals). For example, the external power source 118 can include an external coil 119 that communicates with a corresponding internal coil (not shown) within the implantable pulse generator/receiver 121. The external power source 118 can be portable for ease of use.

During at least some procedures, an external programmer 120 (e.g., a trial modulator) can be coupled to the signal delivery device 111 during an initial procedure, prior to implanting the pulse generator/receiver 121. For example, a practitioner (e.g., a physician, a technician, and/or a company representative) can use the external programmer 120 to vary the modulation parameters provided to the signal delivery device 111 in real time, and select optimal or particularly efficacious parameters. These parameters can include the location from which the electrical signals are emitted, as well as the characteristics of the electrical signals provided to the signal delivery device 111. In a typical process, the practitioner uses a cable assembly 114 to temporarily connect the external programmer 120 to the signal delivery device 111. The practitioner can test the efficacy of the signal delivery device 111 in an initial position (e.g., a specified position, which may be ±5 mm from a particular point on or near the patient's spine). The practitioner can then disconnect the cable assembly 114 (e.g., at a connector 117), reposition the signal delivery device 111, and reapply the electrical modulation. This process can be performed iteratively until the practitioner obtains the desired position for the signal delivery device 111. Optionally, the practitioner may move the partially implanted signal delivery device 111 without disconnecting the cable assembly 114.

After a trial period with the external programmer 120, the practitioner can implant the implantable pulse generator/receiver 121 within the patient 190 for longer term treatment. The signal delivery parameters provided by the pulse generator/receiver 121 can still be updated after the pulse generator/receiver 121 is implanted, via a wireless physician's programmer 125 (e.g., a physician's remote) and/or a wireless patient programmer 124 (e.g., a patient remote). The patient 190 may have control over fewer parameters than does the practitioner.

Figure 1B:
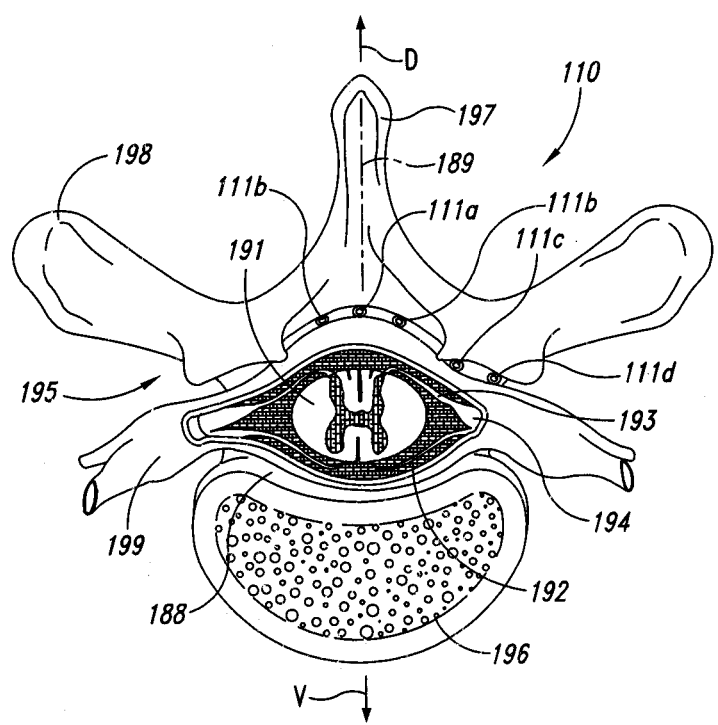
FIG. 1B is a partially schematic, cross-sectional illustration of a patient's spine, illustrating representative locations for an implanted lead in accordance with an embodiment of the disclosure.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple signal delivery devices 111 (shown as signal delivery devices 111a-d) implanted at representative locations. For purposes of illustration, multiple signal delivery devices 111 are shown in FIG. 1B implanted in a single patient. In actual use, any given patient will likely receive fewer than all the signal delivery devices 111 shown in FIG. 1B. As an example, a patient may receive two leads in one or two signal delivery devices 111.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. In one embodiment, a single first signal delivery device 111a is positioned within the vertebral foramen 188, at or approximately at the spinal cord midline 189. In another embodiment, two second signal delivery devices 111b are positioned just off the spinal cord midline 189 (e.g., about 1 mm. offset) in opposing lateral directions so that the two signal delivery devices 111b are spaced apart from each other by about 2 mm. In still further embodiments, a single signal delivery device or pairs of signal delivery devices can be positioned at other locations, e.g., at the dorsal root entry zone as shown by a third signal delivery device 111c, or at the dorsal root ganglia 194, as shown by a fourth signal delivery device 111d.

In any of the foregoing embodiments, it may be useful that the signal delivery device 111 be placed at a target location that is expected (e.g., by a practitioner) or indicated (e.g., by the patient) to produce efficacious results in the patient when activated. The following disclosure describes techniques and systems for improving the level of accuracy with which the devices are positioned.

Figure 2:
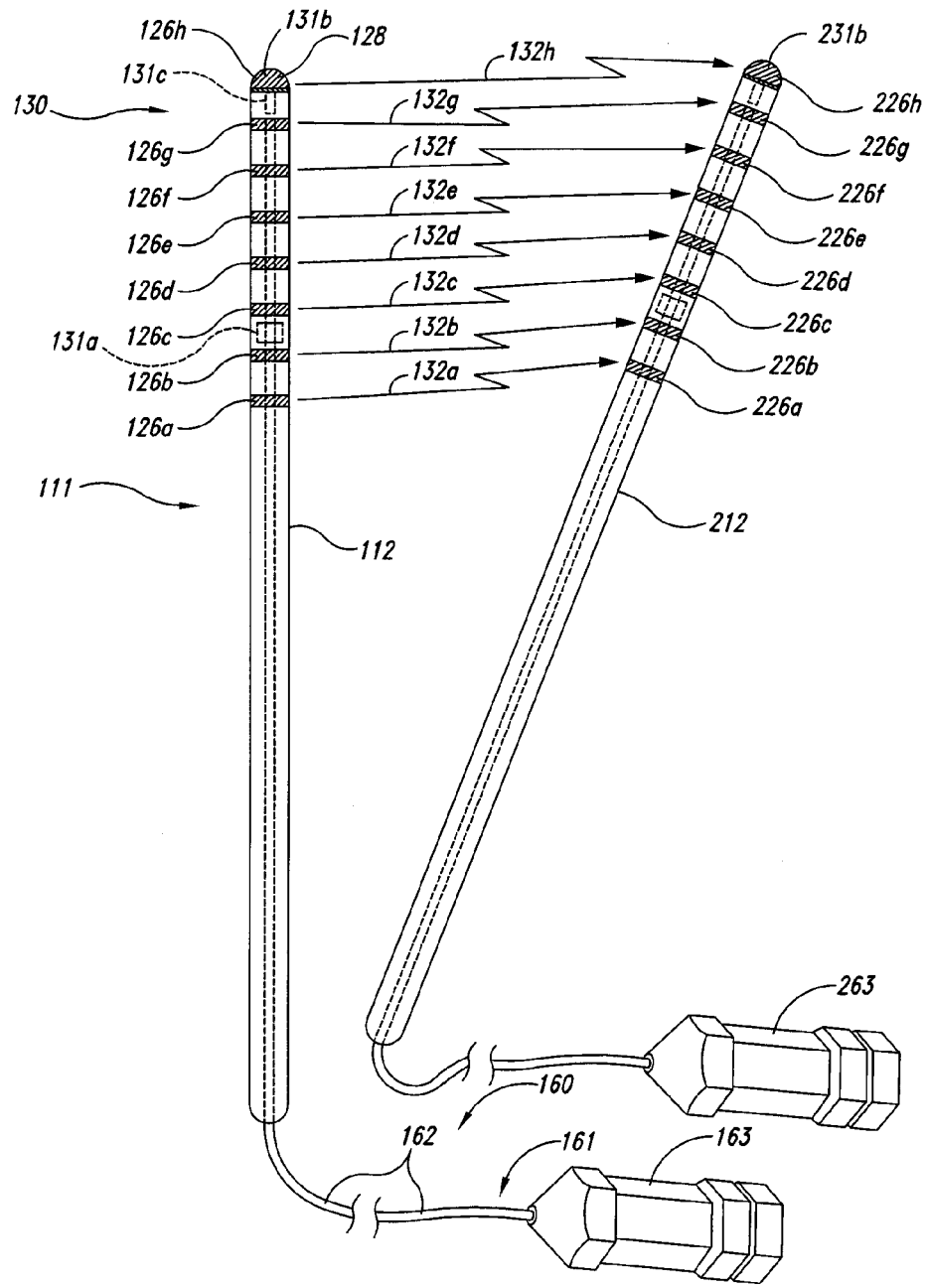
FIG. 2 is a partially schematic illustration of a representative signal delivery device, signal transmission device, and signal detection device, configured in accordance with various embodiments of the disclosure.

FIG. 2 is a partially schematic illustration of a representative signal delivery device, signal transmission device, and signal detection device, configured in accordance with various embodiments of the disclosure. A representative signal delivery device 111 includes leads 112 and 212, each carrying a plurality of ring-shaped therapy contacts. Each contact may transmit and/or receive signals from one or more electrodes. Contacts 126a-h of lead 112 are positioned toward a distal end of lead 112 to deliver a therapy signal to the patient when the lead 112 is implanted. The lead 112 may include internal wires and/or one or more electrodes (not visible in FIG. 2). During implantation, an implanting tool 160 (e.g., a stylet 161) is temporarily coupled to the lead 112 to support the lead 112 as it is inserted into the patient. For example, the implanting tool 160 can include a shaft 162 that is slideably and releasably inserted (via, e.g., a handle 163) into an axially-extending opening in the lead 112. The shaft 162 is generally flexible, but more rigid than the lead 112 to allow the practitioner to insert the lead 112 and control its position during implantation. A stylet stop 128 at the distal end of the lead opening prevents the practitioner from over-inserting the stylet shaft 162. Lead 212 is similar to lead 112. In some embodiments, lead 212 includes a plurality of contacts 226a-h to deliver and/or receive signals. Lead 212 may be adjustable separately from lead 112, e.g., by use of handle 263. In various embodiments, leads 112 and 212 each have eight contacts. In some embodiments, each lead may have a single electrode with multiple contacts or multiple contacts for each of multiple electrodes.

The lead 112 and/or other portions of the overall system 100 can include features that guide the practitioner when positioning the lead 112 at a target location. For example, the signal transmission system 130 can be carried by the lead 112 and/or the implanting tool 160, and can communicate with the signal detector systems located outside the patient's body. Signal transmission devices 131a and 131b can generate, emit, and/or reflect the locator signals 132a-h in a manner that is detected by a signal detector device of a signal detector system. Although eight locator signals 132a-h are illustrated, there may be more or fewer locator signals (even in embodiments with eight contacts per lead). In some embodiments, the signal detector system is lead 212. In other embodiments (not illustrated), the signal detector system may be a system external to the patient. The first signal transmission device 131a can be carried by the lead 112, and can be independent of (e.g., electrically isolated from) the therapy contacts 126. The second signal transmission device 131b can also be carried by the lead 112, but can double as one of the therapy contacts 126. In some embodiments, the second signal transmission device 131b doubles as the distal-most therapy contact 126, located at or near the distal tip of the lead 112. In other embodiments, the second signal transmission device 131b can double as any of the other therapy contacts 126. The third signal transmission device 131c is carried by the implanting tool 160, rather than the lead 112. For example, the third signal transmission device 131c can be located at the distal-most tip of the implanting tool 160.

A patient may respond to treatment differently depending on the relative positions of leads 112 and 212. For example, a patient may experience some relief from pain when lead 212 is at a first position relative to lead 112 and additional relief from pain when lead 212 is at a second position relative to lead 112. The position of a first lead may be determined, e.g., by using technology disclosed in the related application identified in the first paragraph of this patent specification. The relative position of the second lead (e.g., in comparison to the position of the first lead) can be specified using three-dimensional Cartesian coordinates.

The relative position of the second lead as determined by the disclosed technology may also be used to identify leads in a fluoroscopic or other image. Such other images may be ambiguous or difficult to read due to overlap of leads in the image and projection of complex lead geometry into an image plane. In such a case, the disclosed technology may determine that one lead is higher in the epidural canal, thereby enabling unambiguous identification if the image similarly indicates that one lead is positioned higher than the other.

In some embodiments, impedance measurements usable with the disclosed technology may be collected by the implantable pulse generator/receiver 121 or triggered by the wireless physician's programmer 125 or the wireless patient programmer 124. These measurements may be collected regularly, e.g. periodically, or on a schedule determined by physician or patient activity. A series of relative lead positions over time may then be estimated using the methods disclosed herein, correlated to pain or other clinical data indicative of device efficacy, used to predict or constrain future estimates of lead position, and/or displayed to the practitioner.

Figure 3:
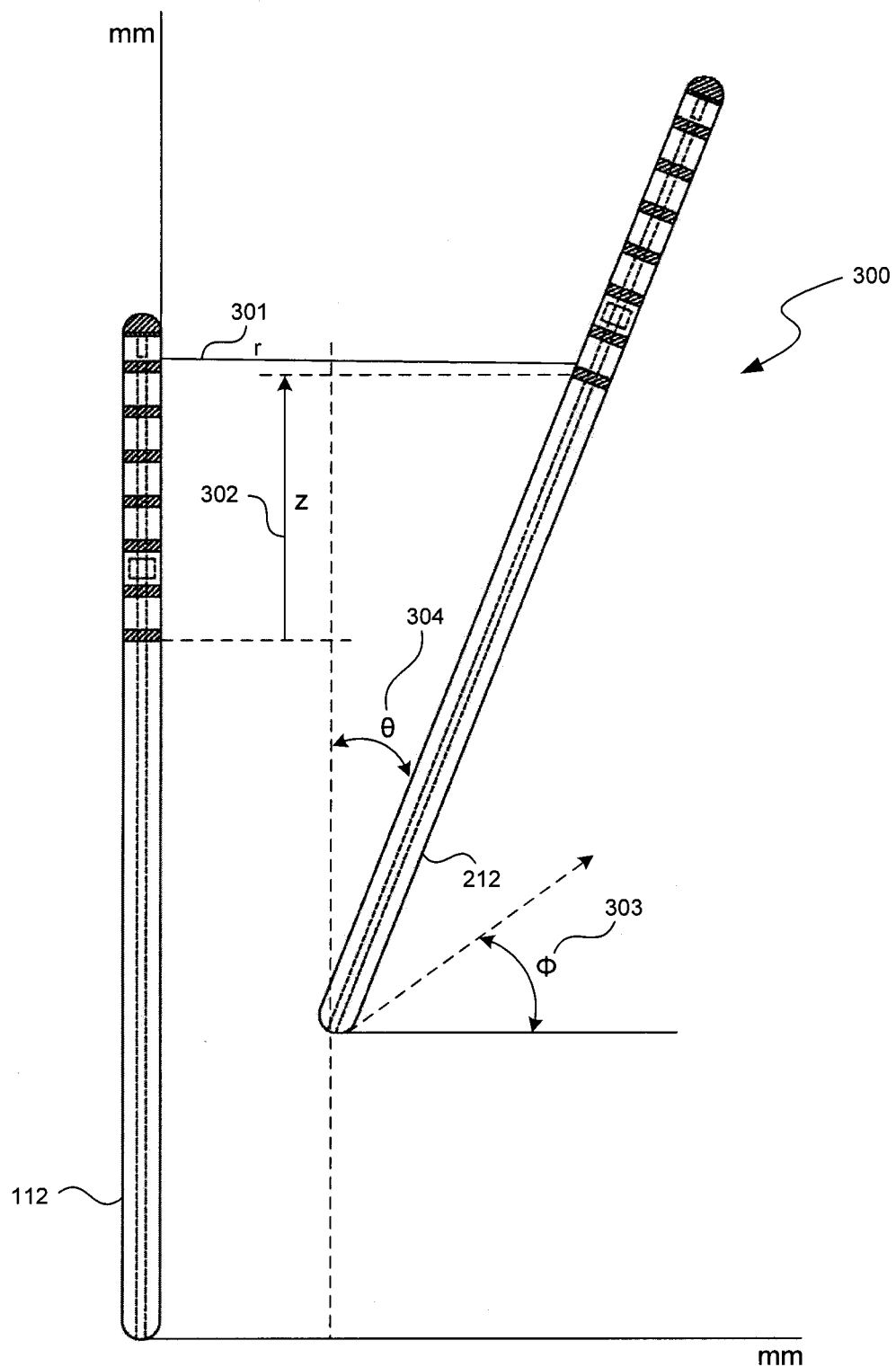
FIG. 3 is a graph diagram illustrating Cartesian coordinates, that can be used in various embodiments of the disclosed technology to identify a position of a second lead relative to a first lead.

FIG. 3 illustrates a forward model 300 that can be used in various embodiments of the disclosed technology, including coordinates used, to identify a position of a second lead relative to a first lead. Taking one end of lead 112 (or a contact of lead 112) as an origin in the coordinate system 300, a parameter z 302 can indicate a z-coordinate of a corresponding end of lead 212 (or a contact of lead 212). A parameter r 301 can indicate a radial distance (e.g., in cylindrical coordinates) between a specified contact on each lead, e.g., a least distal contact from a first end of each lead. Alternatively, parameter r 301 can indicate a radial distance between an axis (e.g., a z-axis) and the corresponding end of lead 212 (or a contact of lead 212). The orientation of lead 212 may also be compared relative to lead 112 in one or more rotational axes. As an example, θ 304 and Φ 303 can indicate, in spherical coordinates, an inclination of lead 212 measured from a zenith located on the z-axis and an azimuth of lead 212 measured counter-clockwise from a plane formed by lead 112 and a contact (e.g., a least distal contact from a first end of lead 212). By using the values r, z, Φ, and θ, the position of the second lead relative to the position of the first lead can be specified highly accurately. Those skilled in the art will appreciate that additional coordinates may be used to describe geometric features, e.g., curvature of the leads; or fewer coordinates may be used, e.g., by assuming an azimuth of zero.

Figure 4:
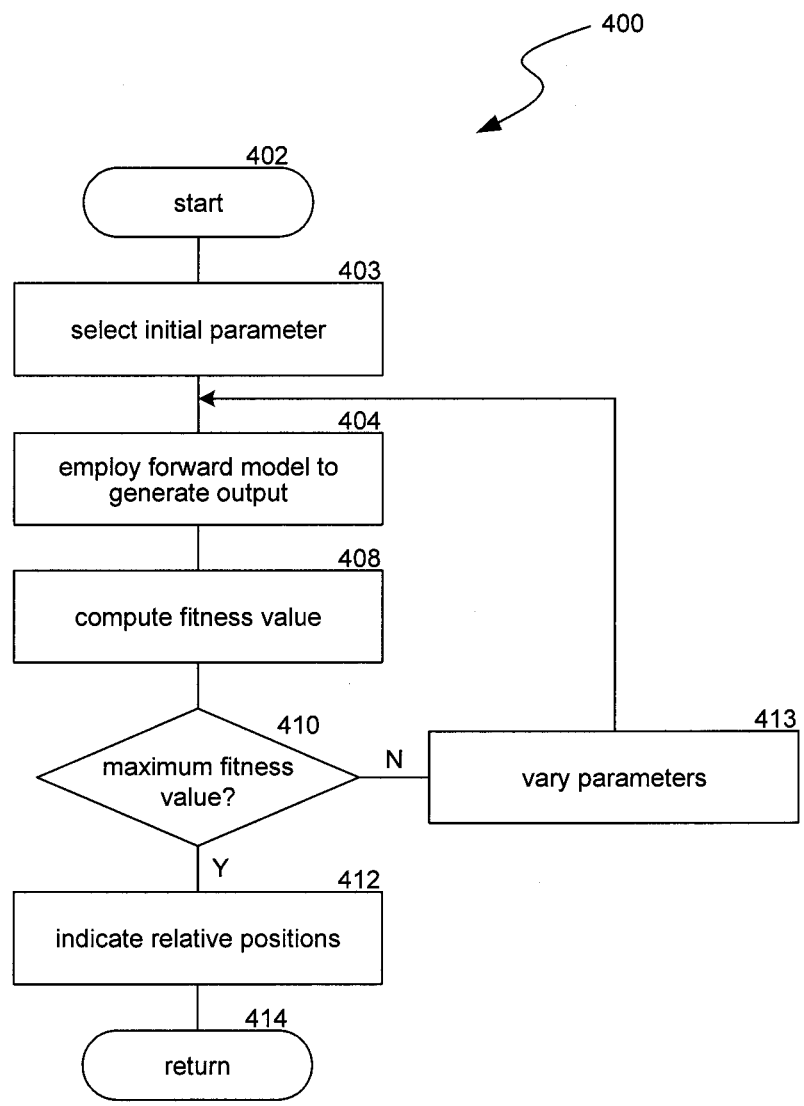
FIG. 4 is a flow diagram illustrating a routine that the disclosed technology may invoke in various embodiments, e.g., to identify a position of a second lead relative to a first lead.

FIG. 4 is a flow diagram illustrating a routine 400 that the disclosed technology may invoke in various embodiments, e.g., to identify a position of a second lead relative to a first lead. The routine 400 begins at block 402.

At block 403, the routine 400 selects an initial parameter or set of parameters, e.g., r=0.2 centimeters; z=Φ=θ=0; and $R_j$ equal to measured or detected one-to-many-contacts impedance values, e.g., for each contact j. These initial parameters may represent a lead position believed to be most likely; they may be based on previous lead position and impedance estimates, or measurements; or may be selected randomly from a physically plausible range of parameters. Those skilled in the art will appreciate that a population of parameter sets may be selected at block 403, each member of the population representing a point in the solution space, and additional steps may be applied to each member of the population to facilitate solution using a population-based algorithm such as a genetic algorithm. As an example, the routine may employ a model to predict expected impedances to each member of the population.

At block 404, the routine 400 employs a model (e.g., a "forward model" 300), e.g., to predict the expected impedances based on a set of parameters supplied to the forward model. Forward modeling techniques can be used to predict one or more values based on observed parameters by applying or varying one or more modeling functions. The forward model takes as parameters r, z, $\Phi$, and $\theta$ that can be used to specify the position of a second lead relative to a first lead. The forward model also takes as parameters impedance parameters $R_j$, e.g., for each contact j of leads 112 and 212. When each lead has eight contacts, j can take on values 1 through 16 and so there would be sixteen impedance values. The impedance parameters can indicate the electrode-tissue impedance at each contact. The impedance parameters $R_j$ may represent the actual electrode-tissue impedance specific to the contact, and can be used to predict the expected impedance between, for example, each contact and a set of other contacts. The impedance parameters $R_j$ may be similar to the predicted, expected impedances and the actual, measured impedances, but they are not necessarily equal to either.

In some embodiments, the impedance between any two contacts j and k is assumed to be the sum of $R_j$, $R_k$, and a function $f(dist_{jk})$ of the Cartesian distance (dist) between the two contacts j and k. The technology can model impedance between one set of one or more contacts and another set of one or more contacts using well known rules for addition of resistances. As an example, the impedance between a contact j and a set of contacts k . . . n can be modeled by Equation (1):

$$R_{total} = R_j + ((R_k + f(dist_{jk}))^{-1} + \ldots + (R_n + f(dist_{jn}))^{-1})^{-1} \quad (1)$$

In various embodiments, the technology may employ more complex or less complex models of electrode-tissue interface impedance and tissue impedance between two electrical contacts. These more complex or less complex models may include characteristics of the electrode-tissue interface impedance and medium impedance such as linearity, nonlinearity, isotropy, anisotropy, or frequency-dependence, other structures affecting impedance such as vertebrae or spinal tissue, or methods such as finite element modeling for calculation of impedances. Equation 1 and/or the function $f(dist_{jk})$ can accordingly be adapted to suit the various embodiments. Quantitative characteristics of these models, such as tissue resistance per unit distance, can also be treated as input parameters to the model and optimized by routine 400.

The forward model can output a set of simulated (e.g., predicted) impedance measurements for each set of parameters r, z, $\Phi$, $\theta$, and $R_j$ (e.g., for each contact j). These simulated impedance measurements may be selected to correspond with actual impedance measurements that have been collected; as an example, if an impedance measurement has been collected between each contact and the set of all other contacts, the forward model can be used to output simulated impedance measurements between each contact and the set of all other contacts.

At block 408, routine 400 computes a fitness value for the selected parameters. A fitness value is a computation of a similarity between the output of the forward model (e.g., the simulated or predicted impedance measurements) and the impedances actually detected or measured. The technology in various embodiments employs a log-likelihood computation for the fitness value. The technology computes the fitness value F of an impedance calculated or predicted by the forward model, $R_{jk-calc}$, in respect to a measured impedance $R_{jk-meas}$ using equation (2):

$$F = -\ln\left(\frac{1}{2(1-L)}\right) \quad (2)$$

where L is a likelihood computed using equation (3):

$$L = 0.5 * \text{erfc}\left(\frac{-|R_{jk-calc} - R_{jk-meas}|}{\sqrt{2}\,\sigma}\right) \quad (3)$$

and where erfc is a complementary error function that is well known in the field of statistics. In equation (3), $\sigma$ is the standard deviation of $R_{jk}$ impedance measurements. The value used for $\sigma$ may be based on the standard deviation of actual impedance measurements or may be selected, e.g., by a practitioner according to clinical conditions, the practitioner's judgment, etc.

Thus, when $R_{jk-calc}$ and $R_{jk-meas}$ are identical, L=0.5 and F=0. Moreover, when $R_{jk-calc}$ and $R_{jk-meas}$ diverge by exactly one standard deviation $\sigma$, L=0.84 and F=−1.148. When L is approximately or effectively equal to 1 because of round-off error, a minimum value can be assigned to F.

Overall fitness for a particular set of outputs from the forward model can be computed by summing F for each calculated versus measured impedance pair. The fitness can be further refined by adding regularization components to favor plausible and parsimonious solutions. As an example, a set of parameters describing a pair of leads positioned at right angles at a great distance from each other may yield the best fit to measured impedance values, due for example to random noise or other sources of measurement error. However, it may be assumed that small angles of inclination $\theta$ are most plausible, all else being equal. An additional term may be added to the fitness computation to express the likelihood of the observed deviation from $\theta$=0. In this way, more unlikely values of r, z, $\Phi$, and $\theta$ can be made to result in more negative fitness values, and in the example above, more plausible solutions may be favored even if the fit to measured values is not perfect.

According to testing completed by the applicants, log-likelihood fitness yields more stable results than some other criteria, e.g., mean-squared error fitness, Cartesian distance criteria, etc. However, in other embodiments, the technology may nevertheless employ mean-squared error or Cartesian distance to evaluate fitness. In some embodiments, the technology may also compute fitness against multiple sets of detected or measured impedances, detected or measured within a relatively short duration, e.g., one clinic visit. In these embodiments, summing the fitness values from each computation may yield an overall fitness value more robust to measurement noise.

At decision block 410, routine 400 may determine whether an optimal fitness value has been computed. A fitness value may be deemed optimal if, for example, it is approximately or substantially equal to zero, if it is greater than a predetermined threshold, or if improvement with successive iterations of routine 400 is less than a predetermined threshold. If an optimal fitness value has been computed, the routine continues at block 412. Otherwise, the routine continues at block 413.

At block 413, routine 400 varies one or more parameters. As an example, the routine 400 may vary r, z, Φ, θ, and $R_j$. In some embodiments, the technology may employ a variant of a simulated metal annealing technique to vary the parameters. An initial set of results can be computed starting from r=0.2 centimeters, z=Φ=θ=0, and $R_j$ selected using measured or detected one-to-many-contacts impedance values, e.g., for each contact j. The "temperature" in the simulated annealing technique can then be gradually decreased over several iterations and at each iteration, a large number of new parameter sets may be generated, randomly perturbing each parameter r, z, Φ, θ, and $R_j$ by an amount proportional to the temperature, e.g., so that the magnitude of the perturbations decreases with each iteration. Prior to proceeding to a subsequent iteration, a specified number of the most fit (e.g., parameter sets resulting in a highest F) can be retained. Parameter sets resulting in less fitness may also be retained, with a probability dependent on "temperature" and diminishing with each iteration. This can result in deriving "more fit" values progressively so that a "most fit" set of parameters can be ultimately identified that maximizes the fitness value. In other embodiments, other techniques can be used to vary parameters. The routine 400 then continues at block 404 where a new output is generated from the forward model based on the parameters varied at block 413.

In various embodiments, the technology may use techniques other than annealing to vary the parameters. These techniques can employ gradients, genetic algorithms, population swarms, etc. One skilled in the art will recognize that various techniques exist to vary parameters and determine an optimal parameter set.

At block 412, routine 400 can indicate the relative positions of the leads or contacts, e.g., on a display. As an example, the technology may render (e.g., display or draw) a graphical depiction of one or both leads on a display so that the practitioner can visually see how the second lead is positioned relative to the first lead, e.g., on a display device. The technology can render changes in position in nearly "real-time" so that the changed positions are evident immediately, e.g., by repeatedly measuring or detecting new impedance measurements, and repeatedly using routine 400 to determine relative lead positions for each new set of impedance measurements.

Those skilled in the art will appreciate that the logic illustrated in FIG. 4 and described above may be altered in a variety of ways. For example, the order of the logic may be rearranged, substeps may be performed in parallel, illustrated logic may be omitted, other logic may be included, etc.

Figure 5:
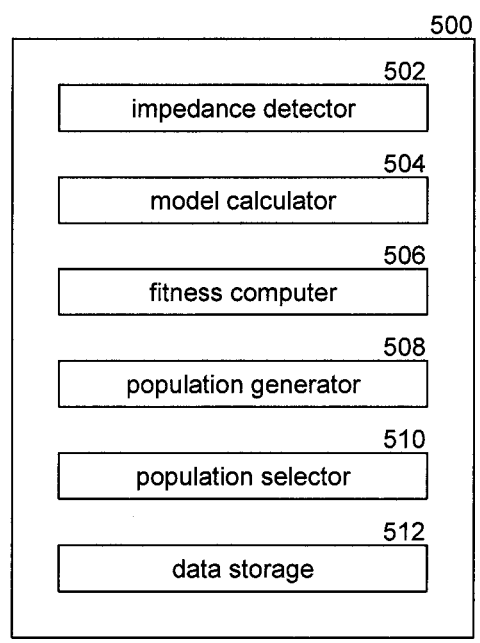
FIG. 5 is a block diagram illustrating components employed by the disclosed technology in various embodiments.

FIG. 5 is a block diagram illustrating components 500 employed by the disclosed technology in various embodiments. In various embodiments, the components 500 may be implemented in hardware, software, or a combination of hardware and software. The components 500 include an impedance detector 502, a model calculator 504, a fitness computer 506, a population generator 508, population selector 510, and data storage 512, e.g., for storing a population of solutions.

Figure 6:
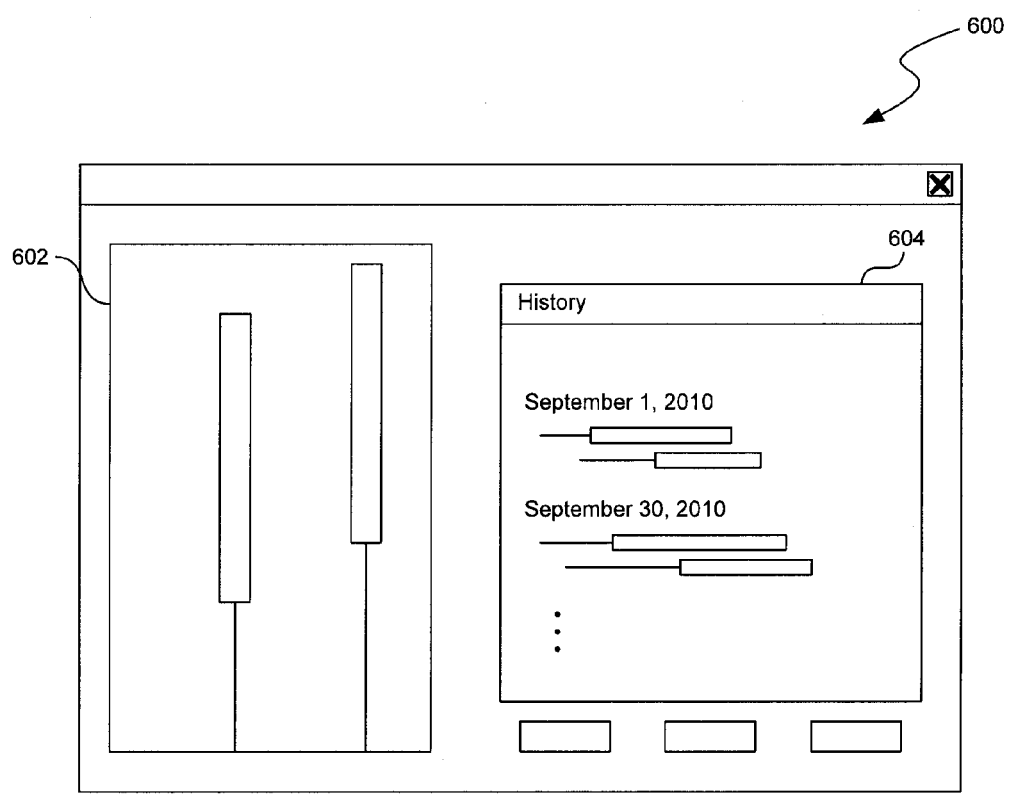
FIG. 6 is a user interface diagram illustrating a user interface implemented by the disclosed technology in various embodiments.

FIG. 6 is a user interface diagram illustrating a user interface implemented by the disclosed technology in various embodiments. In various embodiments, a user interface 600 can include a first region 602 that illustrates a current position of leads; and a second region 604 that illustrates a historical record of lead positions. Various embodiments can include the first region only, the second region only, or both regions. The user interface 600 can be provided at a personal computer, a tablet computer, a small handheld device, etc.

A practitioner may employ the first region 602 to quickly determine relative present positions of leads, e.g., after insertion, and modify parameters, e.g., in response to changes illustrated in the user interface. In various embodiments, region 602 may indicate contacts associated with the leads and impedances detected thereat.

A practitioner may employ the second region 604, e.g., to identify positions at which the patient indicated maximum relief from pain; determine the period of time a patient has been treated; to determine a follow-up routine or schedule, etc.

The user interface 600 can be provided at a clinical environment (e.g., where a patient undergoes treatment), at a home (e.g., in relation to a home monitor), or elsewhere. In various embodiments, the technology can correlate currently observed positions with impedance data changes over time or pain score (e.g., as reported by the patient) changes over time, e.g., to indicate treatment programs or vertebral locations that may need to be re-tested. As an example, the user interface may graphically show regions of the patient's vertebra where treatment has been applied, and results therefrom.

The user interface 600 can be provided in conjunction with implanted pulse generators, trial stimulators, or other devices pertinent to the technology disclosed herein. In various embodiments, the user interface 600 may enable users (e.g., practitioners) to modify parameters, provide alerts (e.g., identify a need for a follow-up visit), record movement of leads, etc.

From the foregoing, it will be appreciated that specific embodiments of the technology have been described herein for purposes of illustration, but that various modifications may be made without deviating from the technology. For example, in other embodiments, the technology can be used to locate devices other than spinal cord implants. In still further embodiments, these devices and methodologies can be applied to implantable patient devices other than neural modulators (e.g., other elements configured for patient implantation, with therapy contacts in at least some cases). The implanting tools described above can have configurations other than a stylet (e.g., a catheter) in other embodiments. The locator signal emitters and/or detectors can be omnidirectional in certain embodiments or can be unidirectional in other embodiments. In certain embodiments, phase shift and/or phased array techniques can be implemented to enhance system efficacy. The signal delivery system can include one transmission device in certain embodiments, and more than one transmission device in other embodiments.

In various embodiments, the leads may have more or fewer than eight contacts or two leads. In various embodiments, the leads may have different shapes, e.g., cylindrical, conical, toroidal, etc. Although the position of the contacts are illustrated as being equally spaced, other embodiments may space the contacts in different positions and orientations.

In various embodiments, the forward model may employ finite elements or other techniques, e.g., to more accurately estimate impedances. Although the embodiments described above assume that human tissue is homogeneous, e.g., for prediction of impedances, other forward models may not make this assumption and may take account of inhomogeneous or anisotropic tissue models.

In some embodiments, the technology may take account of the spinal anatomy of the patient. As an example, the forward models that the technology may employ may vary depending on the presence or absence of tissue, bone, etc., so that impedances can be predicted more accurately. In some embodiments, parameters describing the position of leads with respect to these anatomical structures may be included in the forward model and optimization process, yielding a determination of position with respect to these structures in addition to a determination of relative lead position.

In various embodiments, the technology may include for consideration impedances measured at various points, e.g., various arbitrary points associated with the system in proximity to the patient.

In various embodiments, the leads may be deformed because of contact with tissue or bone, repeated use, etc. The technology can adapt to these deformations, e.g., by varying the forward model to include parameters relating to the extent of deformation. Because of these deformations, electrical impedances may vary.

In various embodiments, the technology may employ techniques designed to reduce or eliminate spurious measurements, e.g., by ignoring measured impedances that are outside of expected norms.

Certain aspects of the technology described in the context of particular embodiments may be combined or eliminated in other embodiments. As an example, of parameters r, z, Φ, and θ, the z parameter may be given additional or exclusive consideration as compared to the r, Φ, or θ parameters. In various embodiments, more or fewer parameters may be employed. As an example, tissue impedance may be specifically varied. Further, while advantages associated with certain embodiments have been described in the context of those embodiments, other embodiments may also exhibit such advantages and not all embodiments need necessarily exhibit such advantages to fall within the scope of the present disclosure. Accordingly, the disclosure and associated technology can encompass other embodiments not expressly described or shown herein.

I claim:

1. A method for treating a patient having an implanted signal delivery device located within a vertebral foramen of the patient, said signal delivery device including a first lead carrying at least a first electrical contact and a second lead carrying at least a second electrical contact, said first electrical contact having been positioned relative to a target location, said method comprising:

detecting an electrical impedance between the at least a first contact of the signal delivery device and the at least a second contact of the signal delivery device;

computing a position of the second lead relative to the first lead based at least on the detected electrical impedance;

transmitting at least one locator signal from the signal delivery device;

detecting the at least one locator signal from a position external to the patient; and based at least in part on detecting the at least one locator signal, adjusting a position of the signal delivery device.

2. The method of claim 1, wherein the positioning of the first and the second electrical contacts occurs without use of fluoroscopy.

3. The method of claim 1 further comprising modulating neural activity to reduce patient pain.

4. The method of claim 1 further comprising constructing a forward model.

5. The method of claim 4 wherein the forward model receives as a parameter a value indicating a position of a second contact of a second lead relative to a first contact of a first lead.

6. The method of claim 5 wherein the parameter value is drawn from a continuous range of values.

7. The method of claim 5 wherein the forward model additionally receives as a parameter a radial distance between the first electrical contact and the second electrical contact in a substantially axial direction.

8. The method of claim 5 wherein the forward model additionally receives as a parameter a radial distance between an axis of the first lead and a specified contact of a second lead.

9. The method of claim 5 wherein the forward model additionally receives as a parameter an inclination of a lead.

10. The method of claim 5 wherein the forward model additionally receives as a parameter an electrode-tissue interface impedance at the first and the second electrical contacts.

11. The method of claim 5 further comprising computing a fitness value based on a comparison between the detected electrical impedance and an electrical impedance predicted by the forward model.

12. The method of claim 11 further comprising varying the parameter and iterating computation of electrical impedance and computing the fitness value until a maximum fitness value is computed.

13. The method of claim 12 further comprising rendering a relative position of the second lead on a display device.

* * * * *